(12) United States Patent
Hewlings

(10) Patent No.: US 10,632,158 B2
(45) Date of Patent: Apr. 28, 2020

(54) USE OF A HYPERIMMUNE EGG PRODUCT TO PREVENT AND TREAT DYSBIOSIS

(71) Applicant: IgY Nutrition, Oklahoma City, OK (US)

(72) Inventor: Susan J. Hewlings, Cudjoe Key, FL (US)

(73) Assignee: IGY Nutrition, Oklahoma City, OK (US)

( * ) Notice: Subject to any disclaimer, the term of this patent is extended or adjusted under 35 U.S.C. 154(b) by 0 days.

(21) Appl. No.: 15/631,216

(22) Filed: Jun. 23, 2017

(65) Prior Publication Data

US 2017/0368113 A1 Dec. 28, 2017

Related U.S. Application Data

(60) Provisional application No. 62/353,823, filed on Jun. 23, 2016.

(51) Int. Cl.

| | | |
|---|---|---|
| *A61K 49/00* | (2006.01) | |
| *A61K 39/00* | (2006.01) | |
| *A61K 39/02* | (2006.01) | |
| *A61K 35/747* | (2015.01) | |
| *C07K 16/12* | (2006.01) | |
| *A61K 35/741* | (2015.01) | |
| *A61K 35/742* | (2015.01) | |
| *A61K 35/745* | (2015.01) | |
| *A61K 35/57* | (2015.01) | |

(52) U.S. Cl.
CPC ............ *A61K 35/747* (2013.01); *A61K 35/57* (2013.01); *A61K 35/741* (2013.01); *A61K 35/742* (2013.01); *A61K 35/745* (2013.01); *A61K 39/02* (2013.01); *C07K 16/12* (2013.01)

(58) Field of Classification Search
CPC .. A61K 39/00; A61K 39/0005; A61K 39/395; A61K 39/40
USPC .............................. 424/9.1, 9.2, 184.1, 234.1
See application file for complete search history.

(56) References Cited

U.S. PATENT DOCUMENTS

| | | | |
|---|---|---|---|
| 5,772,999 A * | 6/1998 | Greenblatt | ............. A61K 35/20 424/157.1 |
| 6,420,337 B1 | 7/2002 | Iyer et al. | |
| 6,706,267 B1 | 3/2004 | Adalsteinsson et al. | |
| 6,803,035 B2 * | 10/2004 | Greenblatt | ............. A61K 35/57 424/130.1 |
| 7,083,809 B2 | 8/2006 | Iyer et al. | |
| 9,701,735 B2 | 7/2017 | Starzl | |

OTHER PUBLICATIONS

Cummings, John H., et al., "Gut Health and Immunity", European Journal of Nutrition, 2004, vol. 43 (Suppl 2), p. 1-56.
Zak-Golab, Agnieszka, et al., "Gut Microbiota, Microinflammation, Metabolic Profile, and Zonulin Concentration in Obese and Normal Weight Subjects", International Journal of Endocrinology, 2013, vol. 2013, pp. 1-9.

\* cited by examiner

*Primary Examiner* — Rodney P Swartz
(74) *Attorney, Agent, or Firm* — McCarter & English, LLP

(57) ABSTRACT

Methods for treating and preventing dysbiosis in a subject suffering from or susceptible to gastrointestinal disorders are described. The methods comprises administering a hyperimmunized egg product to the subject, wherein the egg product is obtained from a hyperimmunized avian, optionally in combination with an additional compound such as a probiotic and/or nutrient source.

13 Claims, 4 Drawing Sheets

USE OF A HYPERIMMUNE EGG PRODUCT TO PREVENT AND TREAT DYSBIOSIS

RELATED APPLICATIONS

This application claims priority to U.S. Provisional Patent Application No. 62/353,823 filed on Jun. 23, 2016, the contents of which are incorporated herein in their entirety.

FIELD OF THE INVENTION

This invention relates to methods for treating and preventing dysbiosis in a subject comprising administering a hyperimmune egg product to the subject, optionally in combination with additional compounds such as probiotics and/or nutrient sources.

BACKGROUND OF THE INVENTION

Gut related complaints affect 60-70 million people in the US costing nearly 40 billion dollars in primary care visits alone, excluding procedures and specialists evaluations. Even minor digestive complaints are associated with more time of work and a decreased quality of life. Minor digestive complaints are indicative of low levels of inflammation in the gut, which can contribute to other disorders systemically in which inflammation plays a role. Digestive complaints increase systemic levels of IL-6, IL-8 and TNF alpha. See Zak-Golab et al., 2013, International Journal of Endocrinology: 1-9, Article ID 674106. These mediators of inflammation are implicated in fatigue, weight gain, auto-immune conditions, depression and others. Interventions that can effectively treat gut based inflammation have far reaching implications in patient care management.

Many digestive complaints may be the result of dysbiosis, a microbial imbalance in the gastrointestinal tract. Dysbiosis is a state in which the microbiota produces harmful effects via: (1) qualitative and quantitative changes in the intestinal flora itself; (2) changes in their metabolic activities; and (3) changes in their local distribution. Factors such as antibiotics, psychological and physical stress, and certain dietary components have been found to contribute to intestinal dysbiosis. These factors result in alterations in bacterial metabolism, as well as the overgrowth of potentially pathogenic microorganisms. It is believed the growth of these bacteria in the intestines results in the release of potentially toxic products that play a role in many chronic and degenerative diseases, including irritable bowel syndrome, inflammatory bowel disease, rheumatoid arthritis, and ankylosing spondylitis. See Hawrelak et al., 2004, Altern Med Rev 9(2):180-197.

There is, accordingly, a need for a simple, effective treatment that can alleviate dysbiosis and its role in chronic and degenerative diseases, without the complication of side effects.

SUMMARY OF THE INVENTION

In certain aspects the invention relates to a method for increasing levels of beneficial flora in a subject, the method comprising: administering to the subject an effective amount of a hyperimmunized egg product; and administering to the subject an effective amount of an additional compound selected from the group consisting of a nutrient source and a probiotic, thereby increasing levels of beneficial flora in the subject relative to a subject that is not administered the hyperimmunized egg product and the additional compound. In certain embodiments, the level of beneficial flora is increased relative to a subject that is administered the hyperimmunized egg product, but not the additional compound. In certain embodiments, the level of beneficial flora is increased relative to a subject that is administered the additional compound, but not the hyperimmunized egg product.

In certain embodiments, increasing levels of beneficial flora in the subject comprises decreasing intestinal permeability in the subject relative to a control subject that is not administered the hyperimmunized egg product and the additional compound. In certain embodiments, the subject is afflicted with a disorder selected from the group consisting of Crohn's disease, celiac disease, type 1 diabetes, rheumatoid arthritis, spondyloarthropathies, inflammatory bowel disease, and irritable bowel syndrome.

In certain aspects the invention relates to a method for treating or preventing dysbiosis in a subject, the method comprising: administering to the subject an effective amount of a hyperimmunized egg product; and administering to the subject an effective amount of an additional compound selected from the group consisting of a nutrient source and a probiotic, thereby treating or preventing the dysbiosis in the subject. In certain embodiments, the treating or preventing dysbiosis comprises decreasing intestinal permeability in the subject relative to a control subject that is not administered the hyperimmunized egg product and the additional compound. In certain embodiments, the subject is afflicted with a disorder selected from the group consisting of Crohn's disease, celiac disease, type 1 diabetes, rheumatoid arthritis, spondyloarthropathies, inflammatory bowel disease, and irritable bowel syndrome.

In certain aspects the invention relates to a method of increasing the effectiveness of a probiotic in a subject, the method comprising: administering to the subject an effective amount of a hyperimmunized egg product; concurrently administering to the subject an effective amount of a probiotic; wherein the effectiveness of the probiotic is increased as compared to the effectiveness of a probiotic administered to a subject without the hyperimmunized egg product.

In certain aspects the invention relates to a method of increasing the effectiveness of a nutrient source in a subject, the method comprising: administering to the subject an effective amount of a hyperimmunized egg product; and concurrently administering to the subject an effective amount of a nutrient source; whereby the effectiveness of the nutrient source is increased as compared to the effectiveness of a nutrient source administered to a subject without the hyperimmunized egg product. In certain embodiments, administration of the hyperimmunized egg product and the probiotic or nutrient source reduces zonulin levels in the subject relative to a control subject that is not administered the hyperimmunized egg product and the probiotic or nutrient source. In certain embodiments, the hyperimmunized egg product is obtained by treating an egg-producing animal with a vaccine comprising at least one immunogen from an organism. In certain embodiments, the vaccine consists of a mixture of bacterial immunogens, said mixture comprising at least one immunogen from each of the following bacterial strains: *Escherichia coli, Escherichia coli* (Aerobacter); *Klebsiella pneumonia; Pseudomonas aeruginosa; Salmonella typhimurium; Salmonella dysenteriae; Salmonella enteriditis*; Salmon epidermis; *Salmonella simulans; Streptococcus pyogenes*, type 1; *Streptococcus pyogenes*, type 3; *Streptococcus pyogenes*, type 5; *Streptococcus pyogenes*, type 8; *Streptococcus pyogenes*, type 12; *Streptococcus pyogenes*, type 14; *Streptococcus pyogenes*, type 18; *Strep-* tococcus pyogenes, type 22; *Pseudomonas vulgaris*; *Streptococcus agalactiae*; *Streptococcus mitis*; *Streptococcus mutans*; *Streptococcus salavarius*; *Streptococcus sanguis*; *Streptococcus pneumoniae*; *Propionibacterium acnes*; and *Haemophilis influenzae*.

In certain embodiments of the aforementioned methods, the effective amount of the hyperimmunized egg product administered to the subject ranges from 0.5-6 grams of egg product per kilogram of subject weight per day. In certain embodiments, the effective amount of hyperimmunized egg product administered to the subject is 4 grams of egg product per kilogram of subject weight per day. In certain embodiments, the hyperimmunized egg product is administered parenterally, subcutaneously, intravenously, intramuscularly, intraperitoneally, intranasally, orally or topically. In certain embodiments, the probiotic or nutrient source is administered parenterally, subcutaneously, intravenously, intramuscularly, intraperitoneally, intranasally, orally or topically. In certain embodiments, the hyperimmunized egg product and the probiotic or nutrient source are administered to the subject in the same composition. In certain embodiments, the hyperimmunized egg product and the probiotic or nutrient source are administered to the subject in separate compositions. In certain embodiments, the probiotic is selected from the group consisting of *Lactobacillus gasseri* and *Bacilllus coagulans*.

In certain embodiments of the aforementioned methods, the composition comprises one or more compounds selected from the group consisting of Whey Protein Isolate, Whey Protein Concentrate, Egg Powder, Pea Protein, Sunflower Oil Powder, Natural Flavors, Oat Fiber, L-Taurine, Xanthan Gum, Cellulose, LuraLean™ (Glucomannan), Acacia Powder, *Psyllium*, Guar Gum, Salt, L-Carnitine, L-Ornithine, Green Tea Extract Powder, Green Coffee Bean Extract, Caffeine, Moringa Leaf Extract, Amylase, Protease, Cellulase, Lactase, Lipase, Acesulfame-K, Sucralose, Medium Chain Triglycerides Powder, Ascorbic Acid, Mono & Diglycerides, D-Alpha-Tocopheryl Acetate, Biotin, Niacinamide, Vitamin A Palmitate, Copper Amino Acid Chelate, Zinc Oxide, Potassium Iodide, Calcium Pantothenate, Manganese Amino Acid Chelate, Sodium Selenite, Folic Acid, Cholecalciferol, Pyridoxine Hydrochloride, Chromium Chloride, Thiamine Mononitrate, Riboflavin and Cyanocobalamin. In certain embodiments, the composition further comprises cocoa powder. In certain embodiments, the composition further comprises instant coffee.

In certain aspects, the invention relates to a composition comprising a hyperimmunized egg product; and an additional compound selected from the group consisting of a nutrient source and a probiotic. In certain embodiments, the hyperimmunized egg product is obtained by treating an egg-producing animal with a vaccine comprising at least one immunogen from an organism. In certain embodiments, the vaccine consists of a mixture of bacterial immunogens, said mixture comprising at least one immunogen from each of the following bacterial strains: *Escherichia coli*, *Escherichia coli* (Aerobacter); *Klebsiella pneumonia*; *Pseudomonas aeruginosa*; *Salmonella typhimurium*; *Salmonella dysenteriae*; *Salmonella enteriditis*; Salmon epidermis; *Salmonella simulans*; *Streptococcus pyogenes*, type 1; *Streptococcus pyogenes*, type 3; *Streptococcus pyogenes*, type 5; *Streptococcus pyogenes*, type 8 *Streptococcus pyogenes*, type 12; *Streptococcus pyogenes*, type 14; *Streptococcus pyogenes* type 18; *Streptococcus pyogenes*, type 22; *Pseudomonas vulgaris*; *Streptococcus agalactiae*; *Streptococcus mitis*; *Streptococcus mutans*; *Streptococcus salavarius*; *Streptococcus sanguis*; *Streptococcus pneumoniae*; *Propionibacterium acnes*; and *Haemophilis influenzae*.

In certain embodiments of the aforementioned compositions, the composition comprises between 0.01% and 50% w/w of the hyperimmunized egg product.

In certain embodiments, the composition is formulated for parenteral, subcutaneous, intravenous, intramuscular, intraperitoneal, intranasal, oral or topical administration. In certain embodiments, the composition comprises one or more compounds selected from the group consisting of Whey Protein Isolate, Whey Protein Concentrate, Egg Powder, Pea Protein, Sunflower Oil Powder, Natural Flavors, Oat Fiber. L-Taurine, Xanthan Gum, Cellulose, LuraLean™ (Glucomannan), Acacia Powder, *Psyllium*, Guar Gum, Salt, L-Carnitine, L-Omithine, Green Tea Extract Powder, Green Coffee Bean Extract, Caffeine, Moringa Leaf Extract, Amylase, Protease, Cellulase, Lactase, Lipase, Acesulfame-K, Sucralose, Medium Chain Triglycerides Powder. Ascorbic Acid, Mono & Diglycerides, D-Alpha-Tocopheryl Acetate, Biotin, Niacinamide, Vitamin A Palmitate, Copper Amino Acid Chelate, Zinc Oxide, Potassium Iodide, Calcium Pantothenate, Manganese Amino Acid Chelate, Sodium Selenite, Folic Acid, Cholecalciferol, Pyridoxine Hydrochloride, Chromium Chloride, Thiamine Mononitrate, Riboflavin and Cyanocobalamin.

In certain embodiments of the aforementioned compositions, the composition comprises Whey Protein Isolate, Whey Protein Concentrate, Egg Powder, Pea Protein, Sunflower Oil Powder, Natural Flavors, Oat Fiber, L-Taurine, Xanthan Gum, Cellulose, LuraLean™ (Glucomannan), Acacia Powder, *Psyllium*, Guar Gum, Salt, L-Carnitine, L-Ornithine, Green Tea Extract Powder, Green Coffee Bean Extract, Caffeine, Moringa Leaf Extract, Amylase, Protease, Cellulase, Lactase, Lipase, Acesulfame-K, Sucralose, Medium Chain Triglycerides Powder, Ascorbic Acid, Mono & Diglycerides, D-Alpha-Tocopheryl Acetate, Biotin, Niacinamide, Vitamin A Palmitate, Copper Amino Acid Chelate, Zinc Oxide, Potassium Iodide, Calcium Pantothenate, Manganese Amino Acid Chelate, Sodium Selenite, Folic Acid, Cholecalciferol, Pyridoxine Hydrochloride, Chromium Chloride, Thiamine Mononitrate, Riboflavin and Cyanocobalamin.

In certain embodiments of the aforementioned compositions, the composition further comprises cocoa powder. In certain embodiments, the composition further comprises instant coffee.

DESCRIPTION OF THE INVENTION

Figure 1:
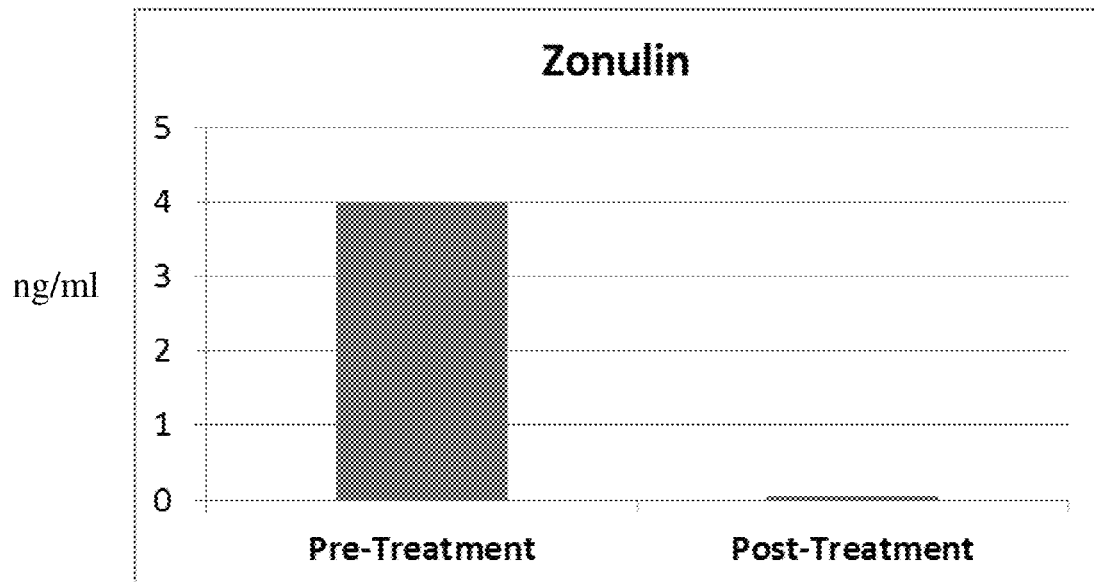
FIG. 1 shows zonulin levels (ng/mL) in patients treated with IgY26.

The hyperimmune egg product of the invention, when administered to a subject, is useful for the treatment and prevention of dysbiosis in that subject, particularly in combination with additional compounds such as probiotics and nutrient sources.

Terminology

The term "probiotic" as used herein refers to a live microbial food ingredient that is beneficial to health. Probiotics include lactic acid producing bacteria such as Lactobacilli and Bifidobacteria, which are commonly used as dairy cultures. In a particular embodiment, the probiotic is selected from *Lactobacillus* gasseri and *Bacillus coagulans*.

The term "beneficial flora" as used herein refers to microorganisms that live in the digestive tract of a subject, for example a human or other animal, and have a positive effect on the health of the subject. Beneficial flora include, but are not limited to, *Bacteroides fragilis, Bifidobacterium* species, *E. coli, Lactobacillus* species, *Enteroccocus* species, and *Clostridium* species.

The term "dysbiosis" as used herein refers to a microbial imbalance in the gastrointestinal tract.

The term "nutrient source" as used herein refers to a source of nourishment especially from a food or food source. Suitable nutrient sources include, but are not limited to, candies, yogurt, protein powder, drinks, meal replacements, and nutritional supplements.

The term "hyperimmunization" means exposure to one or more immunogenics such that an immune response is elevated and maintained above the natural unexposed state.

The terms "egg" or "egg product" each mean any whole egg (table, hyperimmunized or otherwise) or any product or fraction derived therefrom.

The terms "table egg" or "table egg product" each mean a whole egg, or any product or fraction derived therefrom, obtained from egg-producing animals which are not maintained in a hyperimmune state.

The terms "hyperimmune egg" or hyperimmune egg product" each mean whole egg or any product or fraction derived therefrom, obtained from an egg producing animal maintained in a hyperimmune state.

The term "supranormal levels" means levels in excess of those found in eggs of egg-producing animals not maintained in a hyperimmune state.

The term "immunogen" means a substance that is able to induce a humoral antibody and/or cell-mediated immune response rather than immunological tolerance. The term signifies the ability to stimulate an immune response as well as react with the products of it, e.g., antibody.

The term "combinatorial derived immunogens" refers to a novel process of generating molecular diversity among immunogenics by way of combinatorial synthesis.

The term "bioengineered immunogens" refers to immunogens which are obtained through the process of gene cloning technologies and genetic rearrangements which allow the insertion of encoding nucleotides which can give rise to molecules having immunogenicic properties.

The term "genetic vaccine" refers to a nucleic acid vaccine which is generally produced by recombinant technologies and which may elicit an immune response.

The term "treatment" means that the onset of the symptoms (including pain) of the disorder and/or pathogenic origin of the disorder be delayed or completely prevented, or, if present, the symptoms be ameliorated or completely eliminated. For example, the hyperimmune egg product may treat a disorder not only by suppressing the symptoms of the disorder in humans and other mammals, but also by acting as a prophylactic agent to counteract the presence of the disorder in the subject.

The term "prevention" means that the progression of the disease is reduced and/or eliminated, or that the onset of the disease is eliminated.

The term "administer" means any method of providing a subject with a substance, including orally, intranasally, parenterally (intravenously, intramuscularly, or subcutaneously), rectally or topically.

The term "animal" means the animal kingdom definition.

The term "target animal" refers to an animal which functions as the egg or egg product producing animal.

The term "subject animal" refers to the animal which is administered the egg or egg product produced by the target animal.

The methods of the invention relate particularly to the use of hyperimmune egg product, which is a natural food product, in the treatment and prevention of dysbiosis in a subject. Being natural, this food product can be used to treat and prevent dysbiosis without the fear of side effects.

In a preferred embodiment, the hyperimmune egg product is obtained from an egg-producing animal, and more preferably, an avian, which has been hyperimmunized with at least one immunogen. The hyperimmune egg product is one which is preferably administered orally to the subject, although the hyperimmune egg product can be further separated into more potent fractions which can subsequently be administered to a subject in a variety of forms.

The hyperimmunized egg product of the invention, when administered to a subject, is effective in treating and preventing dysbiosis in the subject. In certain embodiments, the hyperimmunized egg product is administered with one or more additional compounds to improve the efficacy of the hyperimmunized egg product in treating dysbiosis. The one or more additional compounds may include, but are not limited to, probiotics and nutrient sources. In certain embodiments, the hyperimmunized egg product and one or ore additional compounds may be used to treat disorders including, but not limited to, Crohn's disease, celiac disease, type 1 diabetes, rheumatoid arthritis, spondyloarthropathies, inflammatory bowel disease, and irritable bowel syndrome.

Hyperimmunized Egg Product

Various genera of the class Aves, such as chickens (*Gallus domesticus*), turkeys, and ducks, produce antibodies in blood and eggs against immunogens that cause avian diseases, as well as against other immunogens. For example, LeBacq-Verheyden et al. (Immunology 27:683 (1974)) and Leslie, G. A., et al. (J. Med. 130:1337 (1969)), have quantitatively analyzed immunoglobulins of the chicken. Polson, A., et al. (Immunological Communications 9:495-514 (1980)) immunized hens against several proteins and natural mixtures of proteins, and detected IgY antibodies in the yolks of the eggs. Fertel, R., et al. (Biochemical and Biophysical Research Communications 102:1028-1033 (1981)) immunized hens against prostaglandins and detected antibodies in the egg yolk. Jensenius et al. (Journal of Immunological Methods 46:63-68 (1981)) provide a method of isolating egg yolk IgG for use in immunodiagnostics. Polson et al. (Immunological Communications 9:475-493 (1980))

describe antibodies isolated from the yolk of hens that were immunized with a variety of plant viruses.

U.S. Pat. No. 4,748,018 discloses a method of passive immunization of a mammal that comprises parenterally administering purified antibody obtained from the eggs of an avian that has been immunized against the corresponding antigen, and wherein the mammal has acquired immunity to the eggs.

U.S. Pat. No. 5,772,999, assigned to DCV-Biologics, discloses a method of preventing, countering or reducing chronic gastrointestinal disorders or Non-Steroidal Anti-Inflammatory Drug-induced (NSAID-induced) gastrointestinal damage in a subject by administering hyperimmunized egg and/or milk or fractions thereof to the subject.

An immunized egg is an egg which comes from an avian which has been immunized with, for example, a specific antigen or mixture of antigens. A hyperimmunized egg is an egg which comes from an avian which has been brought to a specific state of immunization by means of, for example, periodic booster administrations of antigens. Hyperimmunized eggs, no matter the type of antigen their avian maker has been administered, have been found to have various beneficial factors, including, as mentioned above, the treatment of chronic gastrointestinal disorders, NSAID-induced gastrointestinal damage (see U.S. Pat. No. 5,772,999) and anti-inflammatory effects due to the presence of an anti-inflammatory composition (see U.S. application Ser. No. 09/233,379).

The hyperimmunized egg product can be produced by any egg-producing animal. It is preferred that the animal be a member of the class Aves or, in other words, an avian. Within the class Aves, domesticated fowl are preferred, but other members of this class, such as turkeys, ducks, and geese, are a suitable source of hyperimmune egg product.

When such egg-producing animals are brought to a specific state of immunization by means of, for example, periodic booster administrations of immunogenics, the animals will produce eggs having beneficial properties that, when consumed by a subject, such beneficial properties will treat and prevent dysbiosis in that subject.

This special state of hyperimmunization is preferably achieved by administering an initial immunization, followed by periodic boosters with sufficiently high doses of specific immunogens or mixtures of immunogens. The preferred dosage of booster should be equal to or greater than 50% of the dosage necessary to produce primary immunization of the avian. Thus, there is a threshold booster dosage below which the properties are not produced in the avian's egg, even though the avian is in what normally would be called an immune state.

Having knowledge of the requirement for developing and maintaining a hyperimmune state, it is within the skill of the art to vary the amount of immunogenic administered, depending on the egg-producing animal genera and strain employed, in order to maintain the animal in the hyperimmune state.

The hyperimmune state is preferably produced by any immunogen or combination of immunogens. Hyperimmunization is preferably achieved by multiple exposures to multiple immunogens, multiple exposure to single immunogens, or single exposures to libraries of immunogens.

In addition to immunizations with naturally occurring immunogens, immunization may also be accomplished using immunogens which are synthetically derived by combinatorial chemistries. The basic strategy is to assemble multiple combinations of chemical building blocks for producing a population of molecules with diversity. Several methods have recently been developed for solid and solution phase combinatorial synthesis of libraries of oligomers (Fodor, S. et al., Science 251:767 (1991); Houghton, R. et al., Nature 354:82 (1991) as well as small organic molecules (Bunin, B. & Ellman, J., J. Am. Chem. Soc. 114:10997 (1992)). Rapid multiple peptide and oligomer synthesis can serve as a source for combinatorial derived immunogens. Furthermore, an alternative strategy would allow the addition of organic building blocks in combinatorial fashion to a backbone molecule for improved immunogenicity.

Alternative modes of hyperimmunizing egg producing animals can be used in place of immunogenic vaccines and include the use of genetic vaccines. In particular, any DNA construct (generally consisting of a promoter region and an immunogen encoding sequence) will trigger an immune response. Genetic vaccines consist of immunogenic-coding vectors, fragments of naked DNA, plasmid DNA, DNA-RNA immunogens, DNA-protein conjugates, DNA-liposome conjugates, DNA expression libraries, and viral and bacterial DNA delivered to produce an immune response. Methods of DNA delivery include particle bombardment, direct injection, viral vectors, liposomes and jet injection, among others. When applying these delivery methods, much smaller quantities may be necessary and generally result in more persistent immunogen production. When using such genetic processes, the preferred method for introducing DNA into avians is through intramuscular injection of the DNA into the breast muscle.

Methods of DNA delivery include but are not limited to, particle bombardment, direct injection, liposomes, jet injection (Fynan, E. F. et al., Proc. Natl. Acad. Sci. USA 90:11478-11482 (1993)). The nucleic acids that code for known or unknown immunogens, promoter regions (notably CMV cauliflower mosaic virus) and SV40 bacterial origin can be replicated in bacteria to produce plasmid DNA for use in DNA injections. Although several routes of parenteral administration of the DNA are effective in chickens, the preferred method is intramuscular injection to the breast muscle. Vaccine trials are carried out in egg laying avians, preferably chickens. Repeated immunizations are given at one to two week intervals for up to six months.

It is preferred that the amounts of DNA used are generally in the order of 50-300 µg of DNA in saline for direct injection. For particle bombardment, 4-100 µg of DNA co-precipitated onto gold beads by the addition of 2.5 M $CaCl_2$ are preferred. Repeated immunizations can be given intradermally by this method of accelerating DNA coated particles into the live animal.

Hyperimmunization Procedure

The following list of steps is an example of a preferred procedure used to bring an egg-producing animal to a heightened state of immunity from which the resultant hyperimmune egg or egg product can be administered to a subject:

1. Selecting one or more immunogenics.
2. Eliciting an immune response in the egg-producing animal by primary immunization.
3. Administering booster vaccines of immunogens of appropriate dosage to induce and maintain the hyperimmune state.

Step 1:

Any immunogenic or combination of immunogens may be employed as a vaccine. The immunogenics can be bacterial, viral, protozoan, fungal, cellular, or any other substances to which the immune system of an egg-producing animal will respond. The critical point in this step is that the immunogen(s) must be capable of inducing immune and hyperimmune states in the egg-producing animal. Although only a single immunogen may function as the vaccine for the method of the invention, one preferred vaccine is a mixture of polyvalent bacterial and fungal immunogens selected from the following immunogenic families: the enteric bacilli and *Bacteroides*, pneumococci, *Pseudomonas, Salmonella*, Streptococci, bacilli, Staphylococci, *Neisseria*, Clostridia, Mycobacteria, Actinomycetes, Chlamydiae, and *Mycoplasma*. Viral immunogens are preferably selected from the following immunogenic families: adenoviruses, picornaviruses and herpes viruses, although other viral immunogenic families will work.

In an alternative embodiment, a polyvalent vaccine referred to as Series 100 (S-100) is used. The bacteria included in the S-100 vaccine are listed in table 1 of Example 1. This vaccine has been previously described in U.S. Pat. Nos. 5,106,618 and 5,215,746, both assigned to Stolle Research and Development Corporation.

Step 2:

The vaccine can be either a killed or live-attenuated vaccine and can be administered by any method that elicits an immune response. It is preferred that immunization be accomplished by administering the immunogens through intramuscular injection. The preferred muscle for injection in an avian is the breast muscle. Dosage is preferably 0.05-5 milligrams of the immunogenic vaccine. Other methods of administration that can be used include intravenous injection, intraperitoneal injection, intradermal, rectal suppository, aerosal or oral administration. When DNA techniques are used for the hyperimmunization process, much smaller quantities are required, generally 300 micrograms.

It can be determined whether the vaccine has elicited an immune response in the egg-producing animal through a number of methods known to those having skill in the art of immunology. Examples of these include enzyme-linked immunosorbent assays (ELISA), tests for the presence of antibodies to the stimulating immunogens, and tests designed to evaluate the ability of immune cells from the host to respond to the immunogen. The minimum dosage of immunogen necessary to induce an immune response depends on the vaccination procedure used, including the type of adjuvants and formulation of immunogen(s) used as well as the type of egg-producing animal used as the host.

Step 3:

The hyperimmune state is preferably induced and maintained in the target animal by repeated booster administrations of an appropriate dosage at fixed time intervals. The time intervals are preferably 2-8 week intervals over a period of 6-12 months. However, it is essential that the booster administrations do not lead to immune tolerance. Such processes are well known in the art.

Methods of preparing the hyperimmunized egg product are described, for example, in U.S. Pat. No. 6,803,035, which is incorporated by reference herein in its entirety.

In certain embodiments, the immunogen is prepared from a bacterial culture containing one or more of the bacteria shown in Table 1 below. In a particular embodiment, the immunogen comprises all of the bacteria shown in Table 1 below.

TABLE 1

| | |
|---|---|
| *Escherichia coli* | *Escherichia coli* (Aerobacter) |
| *Klebsiella pneumoniae* | *Pseudomonas aeruginosa* |
| *Salmonella typhimurium* | *Salmonella dysenteriae* |
| *Salmonella enteriditis* | *Salmonella epidermis* |
| *Salmonella simulans* | *Streptococcus pyogenes*, type 1 |

TABLE 1-continued

| | |
|---|---|
| *Streptococcus pyogenes*, type 3 | *Streptococcus pyogenes*, type 5 |
| *Streptococcus pyogenes*, type 8 | *Streptococcus pyogenes*, type 12 |
| *Streptococcus pyogenes*, type 14 | *Streptococcus pyogenes*, type 18 |
| *Streptococcus pyogenes*, type 22 | *Pseudomonas vulgaris* |
| *Streptococcus agalactiae* | *Streptococcus mitis* |
| *Streptococcus mulans* | *Streptococcus salavarius* |
| *Streptococcus sanguis* | *Streptococcus pneumoniae* |
| *Propionibacterium acnes* | *Haemophilis influenzae* |

It is possible to use other hyperimmunization maintenance procedures or combination of procedures, such as, for example, intramuscular injection for primary immunization and intravenous injection for booster injections. Further procedures include simultaneously administering microencapsulated and liquid immunogen, or intramuscular injection for primary immunization, and booster dosages by oral administration or parenteral administration by microencapsulation means. Several combinations of primary and hyperimmunization are known to those skilled in the art.

In certain embodiments, the hyperimmunized egg product comprises antibodies to one or more of the bacteria shown in Table 1. In a particular embodiment, the hyperimmunized egg product comprises antibodies to all of the bacteria shown in Table 1. In a further particular embodiment, the hyperimmunized egg product is IgY26 as described in Example 1 below. In certain embodiments, a whole egg comprises 50-100 mg of IgY.

Processing and Administration

Once the egg-producing animals have been sufficiently hyperimmunized, it is preferred that the eggs from these animals are collected and processed to produce a hyperimmunized egg product in administrable form. Subsequently, the hyperimmunized egg product can be administered to the subject.

The hyperimmunized egg product of the present invention is administered to a subject by any means that treats or prevents dysbiosis in the subject animal. In certain embodiments, administration occurs by directly feeding an egg or any derivative of the egg. Egg and egg yolk are natural food ingredients and are non-toxic and safe.

In certain embodiments, the hyperimmunized egg product is administered as a composition comprising one or more additional compounds (e.g. a probiotic and/or a nutrient source). For example, in one embodiment, the hyperimmunized egg product of the invention is integrated into a dietary supplement. One preferred method for preparing the egg of the invention to be incorporated into a dietary supplement involves drying the egg into an egg powder. Although various methods are known for drying eggs, spray drying is a preferred method. The process of spray drying eggs is well known in the art. Other examples of egg processing include making an omelet, soft or hard-boiling the egg, or, if desired, the egg can be eaten raw or processed as liquid egg. In certain embodiments, additional compounds such as a probiotic and/or a nutrient source are incorporate into the dietary supplement with the hyperimmunized egg product.

The dried egg powder can be incorporated into a variety of nutrient sources, such as candies, nutritional supplements, meal replacements, drinks (e.g. power building drinks, meal replacement drinks), protein supplements (e.g. protein powders) and any other nutritional, athlete-associated products (e.g. protein bars). In a preferred embodiment, the nutrient source is not cooked (e.g. not baked). Alternatively, the egg powder can be placed in a capsule form and administered as such.

For example, in certain embodiments the hyperimmunized egg product is administered in a composition comprising one or more of the following ingredients: Proprietary Protein Blend (Whey Protein Isolate, Whey Protein Concentrate, Egg Powder, Pea Protein), Sunflower Oil Powder, Natural Flavors, Oat Fiber, L-Taurine, Xanthan Gum, Cellulose, Acacia Powder, Psyllium, Guar Gum, Salt, L-Carnitine, L-Omithine, Probiotic Blend (Lactobacillus gasseri, Bacilllus coagulans), Green Tea Extract Powder, SvetolR (Green Coffee Bean Extract), Caffeine (Natural), Moringa Leaf Extract, Enzyme Blend (Amylase, Protease, Cellulase, Lactase, Lipase), Acesulfame-K, Sucralose, Medium Chain Triglycerides Powder, Ascorbic Acid, Mono & Diglycerides, D-Alpha-Tocopheryl Acetate, Biotin, Niacinamide, Vitamin A Palmitate, Copper Amino Acid Chelate, Zinc Oxide, Potassium Iodide, Calcium Pantothenate. Manganese Amino Acid Chelate, Sodium Selenite, Folic Acid, Cholecalciferol, Pyridoxine Hydrochloride, Chromium Chloride, Thiamine Mononitrate, Riboflavin and Cyanocobalamin. In certain embodiments, the composition comprising the hyperimmunized egg product further comprises Luralean™. Luralean™ is a refined glucomannan (a water-soluble polysaccharide that is considered a dietary fiber) that promotes weight loss in overweight individuals. When used as a dietary supplement, Luralean™ interacts with liquid in the stomach to swell to nearly 200 times its original size. In certain embodiments, the composition further comprises cocoa powder and/or instant coffee. In certain embodiments, the composition is a shake, for example, a weight management shake. In a particular embodiment, the composition comprises all of the aforementioned ingredients. In a further particular embodiment, the composition comprises all of the aforementioned ingredients except instant coffee. In a further particular embodiment, the composition comprises all of the aforementioned ingredients except cocoa powder and instant coffee.

Finally, it is generally known in the art that the yolk and/or white fractions contain the agent or agents responsible for the beneficial properties observed and referred to above. Those having ordinary skill in the art would clearly recognize that further separation could provide more potent fractions or elimination of undesirable components, and would allow for other modes of administration such as administering egg product parenterally, subcutaneously, intravenously, intramuscularly, intraperitoneally, intranasally, orally or topically. Such further separation will provide for the ability to make encapsulated products and pharmaceutical compositions with said egg or fraction thereof.

When it comes to treatment and prevention of dysbiosis, the hyperimmune egg product is preferably administered to the subject in an amount that is immunologically effective in treating and preventing the particular disorder. Dosage and duration of the administration will depend upon the particular condition, whether it is present, and, if so, the advancement of the condition in the subject. It is preferred that the hyperimmune egg product is provided in whatever amount is necessary and effective in treating and/or preventing the condition and the symptoms of the condition. For example, in some cases, daily amounts ranging from less than one to several whole, hyperimmune eggs (or hyperimmune egg products containing the equivalent of less than one to several whole, hyperimmune eggs) can be administered to the subject depending on the particular circumstance of the condition. More potent fractions can be separated and concentrated by methods well-known in the art, from several hundred eggs.

In certain embodiments, the effective amount of the hyperimmunized egg product administered to a subject is 0.1, 0.2, 0.3, 0.4, 0.5, 0.6, 0.7, 0.8, 0.9, 1, 2, 3, 4, 5, 6, 7, 8, 9 or 10 grams per kilogram of subject weight per day. Any of these values may be used to define a range for the effective amount of the hyperimmunized egg product administered to the subject. For example, in some embodiments the effect amount of the hyperimmunized egg product is between 0.1 and 10 grams, between 0.5 to 6 grams, or between 1 and 5 grams per kilogram of subject weight per day.

In certain embodiments, the composition comprises at least 0.01%, 0.05%, 0.1%, 0.5%, 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 96%, 97%, 98% or 99% w/w of the hyperimmunized egg product. Any of these values may be used to define a range for the concentration of the hyperimmunized egg product in the composition. For example, in some embodiments, the composition comprises between 0.01% and 50%, between 0.1% and 50%, or between 1% and 50% w/w of the hyperimmunized egg product.

In certain embodiments, it is desirable to administer the hyperimmune egg in combination with a probiotic (e.g. Lactobacillus gasseri and/or Bacilllus coagulans) or a nutrient source. While not being bound to any theories, it is the inventors' belief that when the hyperimmune egg is administered with, for example, a probiotic, the hyperimmune egg binds to non-beneficial bacteria and as such, prevents them from binding to the gut wall. In turn, this allows for more room for beneficial/good bacteria, such as probiotics, to bind to the gut wall and thrive. In certain embodiments, administration of the hyperimmune egg product in combination with the probiotic or nutrient source has a synergistic effect, for example, in treating or preventing dysbiosis or reducing gut permeability.

In certain embodiments, administration of the hyperimmunized egg product and the probiotic or nutrient source modulates one or more markers of gut permeability. In certain embodiments, the marker of gut permeability is selected from the group consisting of zonulin, diamine oxidase (DAO), and histamine. In certain embodiments, the modulation of the markers of gut permeability comprises one or more of reducing zonulin levels, reducing histamine levels, increasing DAO levels, and increasing the ratio of DAO to histamine in the subject relative to a control subject. In certain embodiments, the control subject is not administered the hyperimmunized egg product and the probiotic or nutrient source. In certain embodiments, the control subject is administered the hyperimmunized egg product, but is not administered the probiotic or nutrient source. In certain embodiments, administration of the hyperimmunized egg product in combination with the probiotic or nutrient source has a synergistic effect on one or more markers of gut permeability.

The egg product of this invention has been shown to be safe, non-toxic, ideal for long term use and has no side effects other than on humans allergic to eggs. The egg product can be orally administered either alone or in combination with drug therapy.

The advantageous properties of this invention can be observed by reference to the following examples that illustrate the invention.

EXAMPLES

Example 1: Preparation of IgY26 Hyperimmunized Egg Product

Preparation of S-100 Vaccine

A bacterial culture containing the spectrum of bacteria shown in Table 1 above, as obtained from the American Type Culture Collection, was reconstituted with 15 mL of media and incubated overnight at 37° C. Once good growth was obtained, approximately one-half of the bacterial suspension was employed to inoculate one liter of broth with the inoculate being incubated at 37° C.

After good growth was visible in the culture, the bacterial cells were harvested by centrifugation of the suspension for 20 minutes to remove the media. The bacterial pellet obtained was resuspended in sterile saline solution and the bacterial sample was centrifuged three times to wash the media from the cells. After the third sterile saline wash, the bacterial pellet was resuspended in a small amount of double distilled water.

The media-free bacterial suspension was killed by placing the suspension in a glass flask in an 80 C water bath overnight. The viability if the broth culture was tested with a small amount of killed bacteria, incubated at 37° C. for five days and checked daily for growth to certify that the bacteria had been killed.

The killed bacteria were lyophilized until dry. The dry bacteria were then mixed with sterile saline solution to a concentration of $2.2 \times 10^8$ bacterial cells/mL saline (1.0 optical density reading at 660 nm). Bacteria contained in the S-100 vaccine are listed in Table 1 above.

Immunization Procedure for IgY26 Hyperimmune Egg Product

A killed preparation of pathogens was prepared as described above. For the first vaccination, the bacteria were mixed with complete Freund's adjuvant, and 5.6 mg of bacterial material were injected into the breast muscle of a chicken. For the remaining vaccines, the bacterial preparation was mixed with incomplete Freund's adjuvant and injected into the chickens at two week intervals for six months.

Eggs were collected from the hyperimmunized chickens and then spray dried into a powder form. During the spray drying procedure, inlet temperatures did not exceed 320° F., exhaust temperatures were maintained in accordance with producing powder in the range of 3.0 to 4.0 percent finished moisture, and pump pressure was maintained around 2500 to 4000 P.S.I. Lower temperatures ranging from 100-160° F. were used, and samples were monitored for moisture content during the drying process to obtain a final IgY26 hyperimmunized egg product having the desired consistency.

Example 2: An Open Label Study to Evaluate the Effects of Immunoglobulin Therapy IgY to Improve Gut Permeability and Quality of Life Objective To evaluate the safety, tolerability, and efficacy of 8 weeks of intervention with IgY26 in subjects who have dysbiosis and a score of 5 or more on a symptom questionnaire. IgY26 is an egg based immunoglobulin that improves gut integrity through reducing gut based inflammation and influencing the microbiome.

Methodology

Initial screening of subjects including symptom screening and physical exam.

Visit 1 (week −2): Obtain informed consent, medical history, screen subjects by individual inclusion and exclusion criteria, routine clinical safety labs Visit 2 (week 0; baseline): Physical exam, studies and vitals and scheduling of final lab work. Patient is advised to once a week check in, and to retain empty bottles of product. Patient is given all product and test kits.

Visit 3 (week 8): Repeat vitals, exit interview from trial, sign forms of completion. Score final questionnaire. Perform blinded statistical analyses.

Six subjects were evaluated, including both male and female subjects. Key inclusion criteria were: male or female; Age: 8 to 80. Patients were selected based on symptom presentation related to gut permeability. Subjects were given a physical examination and vital signs were measured. Subject were required to acknowledge no previous kidney dysfunction or immunologic dysfunction. Subjects were asked to not change their diet, other medications or supplements during the trial.

IgY26 was administered orally in 2 capsules, 2 times per day (i.e. 4 capsules per patient per day), for 8 weeks. Each capsule contains 0.5 g of hyperimmunized egg product (IgY). Thus, this dosage is equivalent to 2 grams of IgY per patient per day.

Patients completed a questionnaire evaluating changes in symptoms before and after treatment. Changes in vital signs (weight, blood pressure, pulse), tenderness with abdominal palpitation, bowels, and quality of life parameters were also measured.

The gut permeability markers zonulin, diamine oxidase (DAO), and histamine were measured in serum to assess gut integrity before and after treatment with IgY. Zonulin levels were measured by zonulin ELISA Kit (Advanced Intestinal Barrier Assessment 5150 Dunwoody Labs, Dunwoody, Ga.). Modulated levels of these markers are associated with less gut damage and better function as well as reduction in certain auto-immune disorders, neurological disorders, and some cancers. For example, zonulin regulates tight junctions in the gut mucosa, and is the gate keeper of gut permeability. Reducing zonulin levels reduces the phenomenon of leaky gut. DAO is a marker of mucosal maturation. Conditions such as Celiac's, Chrohn's disease and colitis are associated with lower levels of diamine oxidase. DAO is an enzyme produced by the microvilli that degrades histamine. Thus DAO plays a role in gut health by controlling conditions that are histaminergic such as rashes, bronchospasms, headaches, anxiety and insomnia. For example, an increased ratio of DAO to histamine is indicative of increased gut health.

Figure 2:
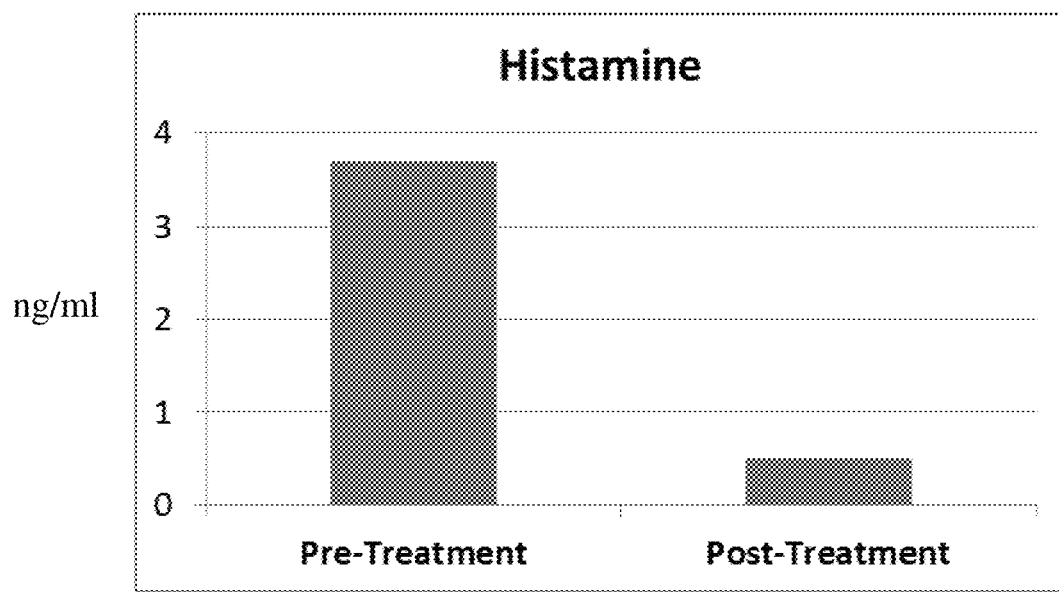
FIG. 2 shows histamine levels (ng/mL) in patients treated with IgY26.
Figure 3:
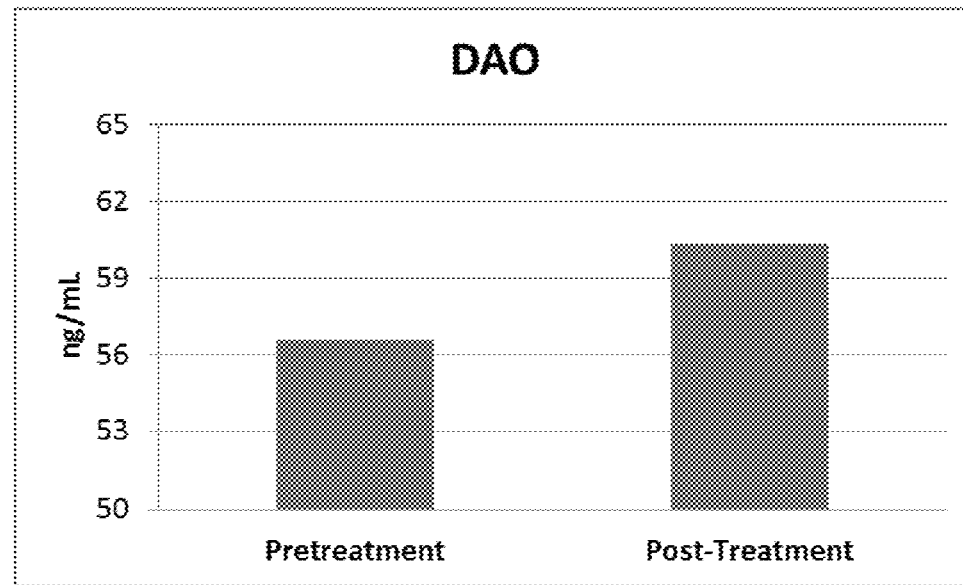
FIG. 3 shows diamine oxidase (DAO) levels (ng/mL) in patients treated with IgY26.
Figure 4:
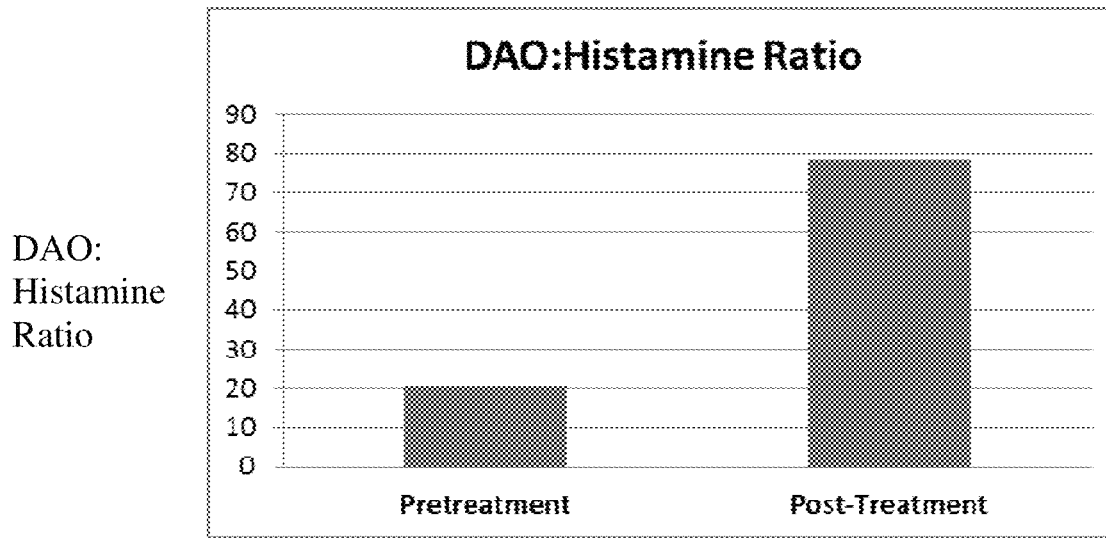
FIG. 4 shows the ratio of diamine oxidase (DAO) to histamine in patients treated with IgY26.
Figure 5:
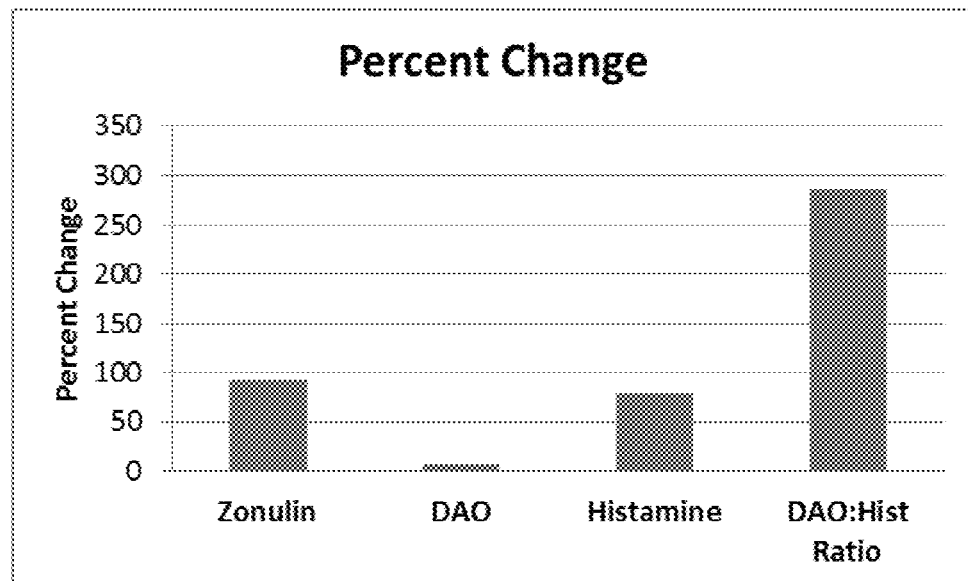
FIG. 5 shows the percent change (increase or decrease) in the gut permeability markers zonulin, diamine oxidase (DAO) and histamine before and after treatment with 2 g per day of IgY26. The percent change was calculated by dividing the difference between the pre-treatment and post-treatment levels by the pre-treatment level.

IgY treatment reduced zonulin and histamine levels and increased DAO levels, indicating that treatment reduced gut permeability. See FIGS. 1-3. IgY treatment increased the ratio of DAO to histamine. See FIG. 4. The percent changes in zonulin, DAO, histamine and DAO: histamine ration before and after treatment with IgY are provided in FIG. 5.

Figure 6:
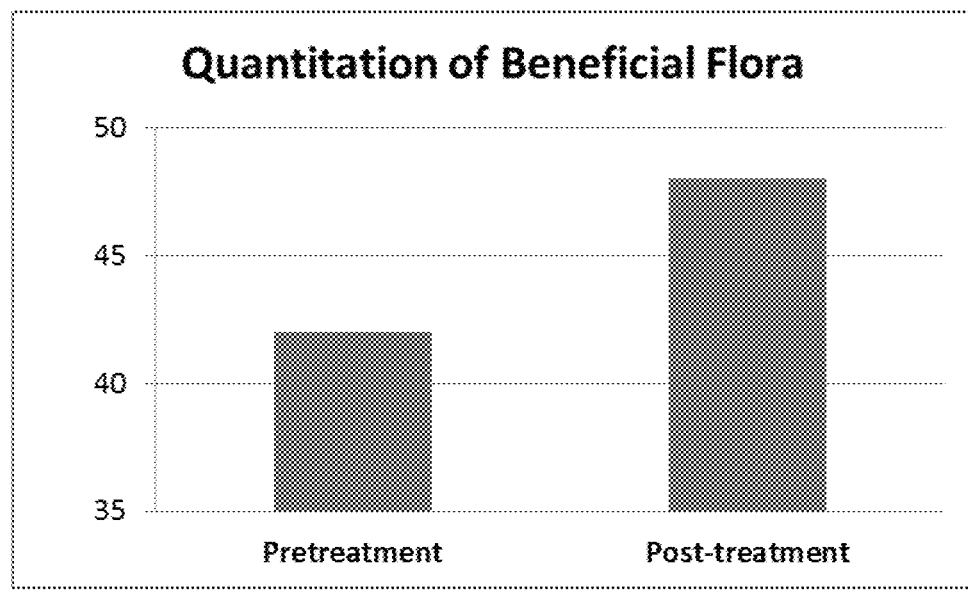
FIG. 6 shows the quantitation of beneficial flora before and after treatment with 2 g per day of IgY26.
Figure 7:
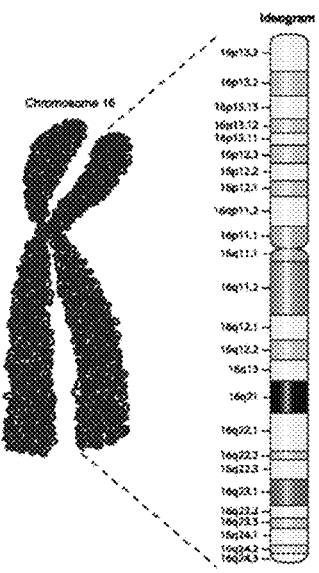
FIG. 7 shows major diseases associated with zonulin (Pre-HP2) and major diseases associated with human chromosome 16.

Three subjects completed a pre and post complete digestive stool culture analysis. There was an overall increase in beneficial flora which was measured on a plus one to plus 4 logarithmic scale. Beneficial flora including *Bacteroides fragilis, Bifidobacterium* species, *E. coli, Lactobacillus, Enteroccocus,* and *Clostridium* were tracked. When the quantitative value of the flora was summed, there was an increase overall after treatment. See FIG. 6. The type of beneficial flora that was most consistently increased was *Lactobacillus*, showing IgY26 to be a unique prebiotic support for microflora, especially *Lactobacillus*.

Case Reports

Of the six subjects tested, none had adverse reactions or events. Subjects reported noticing "a decrease in gas and bloating," and "feeling more energy." These results show that IgY improved quality of life measures. In addition to the subjective data, the reduced levels of the markers show a decrease in gut permeability in response to IgY treatment.

Example 3: The Effects of a Hyperimmune Egg Product and Probiotics on Blood C-Reactive Protein and Gastrointestinal Symptoms The hyperimmune egg product IgY26 (IgY Max™) is a polyvalent antigen specific IgY product from specifically immunized eggs that targets 26 of the most common human-relevant pathogens. IgY26 supports the role of probiotics and prebiotics by aiding in immune system function and by decreasing harmful bacteria while leaving beneficial bacteria intact (Jacoby, H. Moore, G. Wnorowski, G. Inhibition of diarrhea by immune egg: a castor oil mouse model. Journal of Nutraceuticals, Functional & Medical Foods, 2001; 3(2): 47-53; Chalghoumi R, Théwis A, Beckers Y, Marcq C, Portetelle D, Schneider Y J. Foodborne Pathog Dis. 2009; 6(5):593-604.). IgY26 works by significantly reducing harmful bacterial adhesion and growth in the GI tract, and by helping to minimize inflammation by decreasing cytokines and HSCRP (Chalghoumi R, Théwis A, Beckers Y. Marcq C, Portetelle D, Schneider Y J. Foodborne Pathog Dis. 2009; 6(5):593-604).

The purpose of this study was to determine if the effects of IgY26 taken with a probiotic are increased as compared to IgY26 alone or probiotic alone. Effects of the treatments were evaluated by determining changes in blood CRP (C-Reactive Protein, an inflammatory marker), microbial diversity, overall health and well-being, and gastrointestinal symptoms in a sub-clinical population.

The four treatment groups were as follows:
Group A: probiotic alone, 2 capsules per day
Group B: placebo, 2 capsules per day
Group C: probiotic (2 capsules per day)+IgY26 (4 capsules per day)
Group D: IgY26 alone (4 capsules per day)

Each IgY26 capsule contained 0.5 g of whole egg powder, for a total dose of 2 g of whole egg powder per day. Each placebo capsule contained 0.5 g of maltodextrin. Each probiotic capsule contained 1.8 mg of iron, 410 mg of HSO Probiotic blend (5 billion colony forming units (CFU)), and 290 mg of ionic plant based minerals. The HSO probiotic blend included *Saccharomyces boulardii*, barley grass, oat grass, *Lactobacillus plantarum, Bacillus subtilis, Lactobacillus paracasei, Bifidobacterium longum, Lactobacillus brevis, Bifidobacterium bifidum, Bifidobacterium breve, Bifidobacterium lactis, Lactobacillus acidophilus, Lactobacillus salivarius, Lactobacillus rhamnosus* and *Lactobacillum casei*.

Capsules were taken at a similar time each day, starting the day of the baseline visit, for four weeks. Subjects were assigned by chance to each treatment group. There were a total of 40 participants in the study, 10 in each treatment group.

Eligibility requirements for participation in the study are provided below.
  Subject is male or female, 18-60 years of age, inclusive.
  Subject has a BMI of 21.00 to 34.99 kg/m2 at the Screening visit.
  Subject is a non-smoker.
  Subject is not allergic to eggs
  Subject has not been previously diagnosed by a medical doctor (MD or DO) with a digestive disease such as: Celiac Sprue, Wheat Allergy, or Gluten Sensitivity or Celiac Disease.
  Subject has complaints of at least one the following, after they eat a meal or between meals (throughout the day) at least twice per week for 6 months prior:
  abdominal pain (unrelated to menses or other known medical conditions),
  abdominal cramps (unrelated to menses or other known medical conditions),
  abdominal distended—feeling/bloating,
  flatulence,
  Headaches,
  Unclear thoughts (mental clarity, as related to "foggy mind")
  Subject is willing to follow study program instructions.
  Subject is willing and able to comply with the visit schedule.
  Judged to be in good health on the basis of medical history questionnaire, screening physical and screening laboratory assessments.
  Subjects with elevated cholesterol or hypertension on a stable dose of medication may be allowed in the study per PI discretion (stable dose; same dose for 90 or more days).
  Subject understands the study procedures and signs forms providing informed consent to participate in the study and authorization for release of relevant protected health information to the study Investigators.

Each subject participated in a screening visit, baseline visit, and final visit as described below.
  Screening Visit:
  Review of demographic data (including age, gender, race/ethnicity)
  Review of medical history (including diseases, procedures and treatments)
  Review of current medications and supplements (including prescription, over-the-counter medicines, natural health products and functional foods)
  Review of current health conditions including allergies/food allergies.
  Weight, and height measurements and calculation of body mass index (BMI)
  Vital sign measurements (blood pressure, heart rate, temperature, respiratory rate)
  Discuss how to record bowel habits/questionnaire daily for the duration of the study (to be completed daily for two weeks before a subject is administered the study product and for the four weeks during the study)
  Review of study protocol
  Signed informed consent if the subject chooses to participate
  Baseline Visit
  Review of completed food records and diaries
  Questionnaire on gastrointestinal symptoms and overall health (attached)
  Stool sample collection
  Administration of study product
  Blood draw for CRP (~1 tablespoon at study visits 2 and 3)*
  Scheduled next visit
  Final Visit
  Review of completed food records and diaries
  Questionnaire on gastrointestinal symptoms and overall health (attached)
  Stool sample collection
  Blood draw for CRP (~1 tablespoon at study visits 2 and 3)*

In addition to the study visit procedures, subjects were asked to:
  Maintain usual activity level for the duration of the study
  Maintain usual dietary/eating habits for the duration of the study except for exclusionary foods (foods containing prebiotics or probiotics). Subjects received a listing of some of these foods as a reference.
  Collect a stool sample at baseline visit and at end of the study visit.
  Record foods eaten (time, type and amount), for three days before the first stool sample collection Eat the same foods (type, and if possible amount) as those eaten for the three days before the first stool sample collection prior to the last stool sample collection Record bowel habits/questionnaire daily for the duration of the study (completed daily for two weeks before subjects were administered the study product and for the four weeks during the study)

Blood samples for C-reactive Protein (CRP) analysis were drawn from a vein with a sterile needle (usually in the arm) for screening and at the end of study/early termination visit. Stool Samples were collected in Cary-Blair transport medium, Total-Fix® transport medium and a clean vial with no additives (Medical Chemical Corporation, CA). Each subject was provided a stool sample container(s) or vial, gloves, a biohazard container/bag, a tongue depressor or wooden stick and a collection/catching device (hat shaped white plastic). Once received, the stool was cultured for bacteria and yeast on nine plating media (Cary-Blair transport medium), examined for ova and parasites (Total-Fix®) and chemistry analysis (clean vial) to determine effects of the treatments on microbial diversity. Doctor's Data, Inc. microbiology and parasitology subscribe to College of American Pathology (CAP) and Wisconsin State Laboratory of Hygiene (WSLH) proficiency testing programs.

Results

Gastro Intestinal Quality of Life Index (GIQLI)

Preliminary results from 19 subjects in the study are provided below. These subjects include 15 female and 4 male subjects. Subjects were an average of 28.6±10.9 years old and had an average BMI of 26.9±5.9. Response to the treatments was assessed by the Gastro Intestinal Quality of Life Index (GIQLI), a questionnaire containing 36 questions each with five response categories (0, 1, 2, 3 or 4; least desirable option=0; most desirable option=4). The responses to questions are summed to provide a numerical score, with a higher score indicating a greater quality of life. See Eypasch et al., 1995, British Journal of Surgery 82: 216-222. The 36 questions are divided into four different domains based on the subject matter of the question, i.e. the symptomatic domain (questions 1-9 and 27-36), the emotions domain (questions 10-14), the physical domain (questions 15-21), and the social domain (questions 22-23 and 25-26). Question 24 is a clinical question and was omitted from the total score.

The greatest change in total GIQLI over the four weeks of the study was observed in Group C. For example, Group C total GIQLI increased 18.0 points, while Group A, B and D exhibited increases in total GIQLI of 17.00, 12.25, and 11.0, respectively. The changes in GIQLI over the course of the study for individual subjects is shown in Table 2 below.

TABLE 2

Changes in Total GIQLI over four weeks.

| Group C Average Increase | +18 | ↑ | 23.1% |
|---|---|---|---|
| Group C | +28 | ↑ | 35% |
| Group C | +3 | ↑ | 4.1% |
| Group C | +24 | ↑ | 25.8% |
| Group C | +17 | ↑ | 27.4% |
| Group A Average Increase | +17 | ↑ | 20.4% |
| Group A | +3 | ↑ | 3.5% |
| Group A | +48 | ↑ | 57.1% |
| Group A | +9 | ↑ | 12.7% |
| Group A | +8 | ↑ | 8.25% |
| Group B Average Increase | +12.2 | ↑ | 11.7% |
| Group B | +12 | ↑ | 11.6% |
| Group B | +3 | ↑ | 2.6% |
| Group B | +14 | ↑ | 12.6% |

TABLE 2-continued

Changes in Total GIQLI over four weeks.

| Group B | +20 | ↑ | 20% |
|---|---|---|---|
| Group D Average Increase | +11 | ↑ | 14.9% |
| Group D | +8 | ↑ | 6.7% |
| Group D | +3 | ↑ | 2.8% |
| Group D | +29 | ↑ | 46.8% |
| Group D | +4 | ↑ | 3.5% |

Blood C-Reactive Protein (CRP)

Blood C-reactive protein (CRP), an inflammation marker, was also measured in these subjects to determine whether the treatments decreased inflammation. CRP is considered normal at values <1.0 mg/L, and a decrease in CRP levels is indicative of decreased inflammation. Pre-Study and Post-Study blood CRP levels for all groups was >1.0 mg/L. The greatest decrease in blood CRP was observed in Group C. Group C blood CRP decreased −2.8750 mg/L. Group A and D also showed decreases in blood CRP (−1.8250 mg/L and −1.6500 mg/L, respectively). The placebo group, Group B, showed an increase in blood CRP (+1.5000 mg/L). The data for changes in CRP over the course of the 4 week study are shown in Table 3 below.

TABLE 3

Changes in blood C-reactive protein (CRP), pre-study and post-study.

| Group | PreCRP | PostCRP | DiffCRP |
|---|---|---|---|
| A | 3.8000 | 1.9750 | −1.8250 |
| B | 2.9250 | 4.4250 | +1.5000 |
| C | 5.1750 | 2.3000 | −2.8750 |
| D | 4.5750 | 2.9250 | −1.6500 |

These results show that the combination of probiotic and IgY26 (treatment Group C) had the greatest effect in improving gastrointestinal symptoms and reducing inflammation, compared to IgY26 alone (Group D), probiotic alone (Group A), or placebo (Group B).

Fecal Data

Shown below are the results of a preliminary comprehensive stool analysis taken before and after 4 weeks of supplementation. Sixteen subjects from the study are included in the preliminary results. Analyses were conducted by Doctors Data Inc. to assess changes in microbial diversity. Samples were analyzed using MALDI-TOF MS, a proteomic technique that identifies bacteria and yeast by spectral analysis of microorganisms' predominant ribosomal proteins. MALDI-TOF MS enables rapid and accurate identification of normal and pathogenic gastrointestinal microorganisms based upon their signature high-abundance proteins.

The samples were analyzed for the abundance of beneficial flora, imbalanced flora and dysbiotic flora. The number of beneficial flora is the most important aspect to consider when examining the microbial diversity. There are 6 categories examined with a score of 0-4, with 4 being the best (i.e. the highest level of beneficial flora). The scores from each of the six categories was added together, for a total possible score of 24. A score of 12 or less would be indicative of dysbiosis, with a total score of greater than 12 being desirable. A low score for beneficial flora is more telling of dysbiosis than a measure of the dysbiotic flora. The imbalanced flora category could also be called the opportunistic flora in that they typically are not problematic unless there are not enough beneficial flora. There is no upper limit for the imbalanced flora. These flora are transient and can change day to day depending highly on diet.

Subjects administered the combination of probiotic and IgY26 (treatment Group C) exhibited the greatest increase in beneficial flora (+3.3), while IgY26 alone (Group D) exhibited a much smaller increase (+0.75), and probiotic alone (Group B) exhibited a decrease (−1.0). See Table 4 below. Accordingly, these results demonstrate that the combination of probiotic and IgY26 had a synergistic effect on increasing beneficial flora. The placebo exhibited the greatest decrease in beneficial flora for all treatment groups.

TABLE 4

Changes in beneficial flora before and after 4 week treatment with supplements.

| | |
|---|---|
| Group C Average Change Beneficial Flora | +3.3 ± 1.2 |
| Group C | +4 |
| Group C | +4 |
| Group C | +2 |
| Group A Average Change Beneficial Flora | −1.0 ± 2.5 |
| Group A | −1 |
| Group A | −4 |
| Group A | +2 |
| Group A | −3 |
| Group A | +1 |
| Group B Average Change Beneficial Flora | −1.7 ± 3.8 |
| Group B | −1 |
| Group B | +3 |
| Group B | −6 |
| Group B | −3 |
| Group D Average Change Beneficial Flora | +.75 ± 4.3 |
| Group D | 0 |
| Group D | +4 |
| Group D | −5 |
| Group D | +4 |

I claim:

1. A method for increasing levels of beneficial flora in a subject, the method comprising:
   (a) administering to the subject an effective amount of an egg product; and
   (b) administering to the subject an effective amount of an additional compound selected from the group consisting of a nutrient source, and a probiotic,
   thereby increasing levels of beneficial flora in the subject relative to a subject that is not administered the egg product and the additional compound,
   wherein the egg product is obtained from an avian that has been immunized with periodic booster administrations of bacterial antigens and an adjuvant at 2 to 8 week intervals over a period of 6 to 12 months,
   wherein the bacterial antigens comprise the following bacterial strains: *Escherichia coli, Escherichia coli* (Aerobacter); *Klebsiella pneumonia; Pseudomonas aeruginosa; Salmonella typhimurium; Salmonella dysenteriae; Salmonella enteriditis*; Salmon epidermis; *Salmonella simulans; Streptococcus pyogenes*, type 1; *Streptococcus pyogenes*, type 3; *Streptococcus pyogenes*, type 5; *Streptococcus pyogenes*, type 8; *Streptococcus pyogenes*, type 12; *Streptococcus pyogenes*, type 14; *Streptococcus pyogenes*, type 18; *Streptococcus pyogenes*, type 22; *Pseudomonas vulgaris; Streptococcus agalactiae; Streptococcus mitis; Streptococcus mutans; Streptococcus salavarius; Streptococcus sanguis; Streptococcus pneumoniae; Propionibacterium acnes*; and *Haemophilis influenzae*,
   and wherein the egg product comprises antibodies to the bacterial strains.

2. The method of claim 1, wherein the subject is afflicted with a disorder selected from the group consisting of dysbiosis, Crohn's disease, celiac disease, type 1 diabetes, rheumatoid arthritis, spondyloarthropathies, inflammatory bowel disease, and irritable bowel syndrome.

3. A method of increasing the effectiveness of a probiotic in a subject, the method comprising:
   administering to the subject an effective amount of an egg product; and
   concurrently administering to the subject an effective amount of a probiotic;
   wherein the effectiveness of the probiotic is increased as compared to the effectiveness of a probiotic administered to a subject without the egg product, and
   wherein the egg product is obtained from an avian that has been immunized with periodic booster administrations of bacterial antigens and an adjuvant at 2 to 8 week intervals over a period of 6 to 12 months,
   wherein the bacterial antigens comprise the following bacterial strains: *Escherichia coli, Escherichia coli* (Aerobacter); *Klebsiella pneumonia; Pseudomonas aeruginosa; Salmonella typhimurium; Salmonella dysenteriae; Salmonella enteriditis*; Salmon epidermis; *Salmonella simulans; Streptococcus pyogenes*, type 1; *Streptococcus pyogenes*, type 3; *Streptococcus pyogenes*, type 5; *Streptococcus pyogenes*, type 8; *Streptococcus pyogenes*, type 12; *Streptococcus pyogenes*, type 14; *Streptococcus pyogenes*, type 18; *Streptococcus pyogenes*, type 22; *Pseudomonas vulgaris; Streptococcus agalactiae; Streptococcus mitis; Streptococcus mutans; Streptococcus salavarius; Streptococcus sanguis; Streptococcus pneumoniae; Propionibacterium acnes*; and *Haemophilis influenzae*,
   and wherein the egg product comprises antibodies to the bacterial strains.

4. The method of claim 1, wherein the egg product is administered parenterally, subcutaneously, intravenously, intramuscularly, intraperitoneally, intranasally, orally, or topically.

5. The method of claim 1, wherein the probiotic or nutrient source is administered parenterally, subcutaneously, intravenously, intramuscularly, intraperitoneally, intranasally, orally, or topically.

6. The method of claim 1, wherein the egg product and the additional compound are administered to the subject in the same composition.

7. The method of claim 1, wherein the egg product and the additional compound are administered to the subject in separate compositions.

8. The method of claim 6, wherein the nutrient source comprises one or more compounds selected from the group consisting of Whey Protein Isolate, Whey Protein Concentrate, Egg Powder, Pea Protein, Sunflower Oil Powder, Natural Flavors, Oat Fiber, L-Taurine, Xanthan Gum, Cellulose, Glucomannan, Acacia Powder, *Psyllium*, Guar Gum, Salt, L-Carnitine, L-Ornithine, Green Tea Extract Powder, Green Coffee Bean Extract, Caffeine, Moringa Leaf Extract, Amylase, Protease, Cellulase, Lactase, Lipase, Acesulfame-K, Sucralose, Medium Chain Triglycerides Powder, Ascorbic Acid, Mono & Diglycerides, D-Alpha-Tocopheryl Acetate, Biotin, Niacinamide, Vitamin A Palmitate, Copper Amino Acid Chelate, Zinc Oxide, Potassium Iodide, Calcium Pantothenate, Manganese Amino Acid Chelate, Sodium Selenite, Folic Acid, Cholecalciferol, Pyridoxine Hydrochloride, Chromium Chloride, Thiamine Mononitrate, Riboflavin, and Cyanocobalamin.

9. The method of claim 1, wherein the additional compound is a probiotic.

10. The method of claim 6, wherein the composition is a capsule.

11. The method of claim 3, wherein the egg product and the probiotic are administered to the subject in the same composition.

12. The method of claim 11, wherein the composition is a capsule.

13. The method of claim 1, wherein the nutrient source comprises one or more compounds selected from the group consisting of Whey Protein Isolate, Whey Protein Concentrate, Egg Powder, Pea Protein, Sunflower Oil Powder, Natural Flavors, Oat Fiber, L-Taurine, Xanthan Gum, Cellulose, Glucomannan, Acacia Powder, *Psyllium*, Guar Gum, Salt, L-Carnitine, L-Ornithine, Green Tea Extract Powder, Green Coffee Bean Extract, Caffeine, Moringa Leaf Extract, Amylase, Protease, Cellulase, Lactase, Lipase, Acesulfame-K, Sucralose, Medium Chain Triglycerides Powder, Ascorbic Acid, Mono & Diglycerides, D-Alpha-Tocopheryl Acetate, Biotin, Niacinamide, Vitamin A Palmitate, Copper Amino Acid Chelate, Zinc Oxide, Potassium Iodide, Calcium Pantothenate, Manganese Amino Acid Chelate, Sodium Selenite, Folic Acid, Cholecalciferol, Pyridoxine Hydrochloride, Chromium Chloride, Thiamine Mononitrate, Riboflavin, and Cyanocobalamin.

* * * * *